(12) United States Patent
Turner et al.

(10) Patent No.: US 12,329,616 B2
(45) Date of Patent: *Jun. 17, 2025

(54) MOISTURE SENSING GARMENT

(71) Applicant: Bad Little Monster LLC, Fort Collins, CO (US)

(72) Inventors: Debra K. Turner, Garden City, KS (US); Todd C. McCurry, Milliken, CO (US)

(73) Assignee: Bad Little Monster LLC, Colorado Springs, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/240,460

(22) Filed: Aug. 31, 2023

(65) Prior Publication Data

US 2024/0074919 A1   Mar. 7, 2024

Related U.S. Application Data

(63) Continuation of application No. 17/589,447, filed on Jan. 31, 2022, now Pat. No. 11,759,374, which is a continuation of application No. 16/986,422, filed on Aug. 6, 2020, now Pat. No. 11,234,870, which is a continuation of application No. 15/688,663, filed on Aug. 28, 2017, now Pat. No. 10,744,043.

(51) Int. Cl.
  *A61F 13/42*   (2006.01)
  *A61F 13/53*   (2006.01)
  *G08B 21/20*   (2006.01)

(52) U.S. Cl.
  CPC ............. *A61F 13/42* (2013.01); *A61F 13/53* (2013.01); *G08B 21/20* (2013.01)

(58) Field of Classification Search
  CPC .......... A61F 13/15; A61F 13/42; A61F 13/51; A61F 13/513; A61F 13/53; A61F 5/48; G08B 21/00; G08B 21/20; A01L 23/00
  See application file for complete search history.

(56) References Cited

U.S. PATENT DOCUMENTS

| | | | |
|---|---|---|---|
| 10,744,043 | B2 | 8/2020 | Turner et al. |
| 11,234,870 | B2 | 2/2022 | Turner et al. |
| 11,759,374 | B2 | 9/2023 | Turner et al. |
| 2002/0192829 | A1 | 12/2002 | Zainiev et al. |

(Continued)

OTHER PUBLICATIONS

Sprayalert®. Using Alarm to Catch Pet Marking and Help With Dog Training. Website, https://www.sprayalert.com/catch-pet-urine-marking, originally downloaded Feb. 5, 2024, 3 pages.

(Continued)

*Primary Examiner* — Van T Trieu
(74) *Attorney, Agent, or Firm* — Craig R. Miles; CR MILES P.C.

(57) ABSTRACT

A moisture detecting article includes a moisture detection module secured to a garment, intended to contain and hold bodily fluids excreted by an animal. The moisture detection module is connectable to a moisture sensor disposed in the garment to detect when bodily fluid is excreted. If moisture is detected, the moisture sensitive detection module enables one or more signals, alarming the animal and its caretaker. The garment includes a moisture absorbent material, detachable from the garment for disposal of the excretion.

17 Claims, 9 Drawing Sheets

(56) References Cited

U.S. PATENT DOCUMENTS

| | | |
|---|---|---|
| 2003/0132763 A1 | 7/2003 | Ellenz |
| 2004/0220538 A1 | 11/2004 | Panopoulos |
| 2008/0266117 A1 | 10/2008 | Song et al. |
| 2008/0266122 A1* | 10/2008 | Ales .......................... A61F 5/48 |
| | | 340/604 |
| 2012/0256750 A1 | 10/2012 | Novak |
| 2016/0346609 A1 | 12/2016 | Bailly et al. |
| 2019/0246937 A1 | 8/2019 | Chow et al. |

OTHER PUBLICATIONS

U.S. Appl. No. 15/688,663, Office Action mailed Nov. 13, 2019.
U.S. Appl. No. 17/589,447, Office Action mailed Feb. 7, 2023.
The Housebreaker. Stop the Puddles . . . Train the Pup. Website, http://www.thehousebreaker.com, originally downloaded Jun. 14, 2017, 4 pages total.

* cited by examiner

MOISTURE SENSING GARMENT

This United States Patent Application is a continuation of U.S. patent application Ser. No. 17/589,447, filed Jan. 31, 2022, which is a continuation of U.S. patent application Ser. No. 16/986,422, filed Aug. 6, 2020, now U.S. Pat. No. 11,234,870, issued Feb. 1, 2022, which is a continuation of U.S. patent application Ser. No. 15/688,663, filed Aug. 28, 2017, now U.S. Pat. No. 10,744,043, issued Aug. 18, 2020, hereby incorporated by reference herein.

I. FIELD OF THE INVENTION

Generally, embodiments of a moisture detection module and methods for detecting moisture. Specifically, embodiments of a moisture detecting garment including a garment and a moisture detection module secured to a garment. Particular embodiments can be useful in housetraining or monitoring pet animals by detecting body fluids eliminated from the pet animal. The moisture detecting garment can be worn by the pet animal to position moisture sensor to detect elimination of body fluids by the pet animal and provide both the pet animal and the pet caretaker with a warning signal of moisture detection.

II. SUMMARY OF THE INVENTION

A broad object of embodiments can be a moisture detecting article comprising a garment and a moisture detection module secured to the garment. The moisture detection module includes a moisture sensor disposed to sense moisture excreted in the garment, which in turn, generates moisture sensor signals upon occurrence of moisture in the garment. The moisture detection module also includes a processor communicatively coupled to a non-transitory computer readable medium containing computer executable instructions executable to activate at least one moisture indicator, which emits a sensorially perceivable indicia upon detection of the moisture in the garment.

Another broad object of embodiments can be a method of moisture detection in an article. The method comprises securing a moisture detection module to a garment. The moisture detection module includes a moisture sensor and a processor communicatively coupled to a non-transitory computer readable medium containing computer executable instructions. The method further includes disposing the moisture sensor at a location in the garment to sense moisture and initializing the moisture detection module secured to the garment. The computer executable instructions are executable to receive moisture sensor signals generated by the moisture sensor, analyze the moisture sensor signals received from the moisture sensor, detect moisture in the garment based on analysis of the moisture sensor signals, validate detection of the moisture in the garment, and activate a moisture indicator which emits a sensorially perceivable indicia upon detection of the moisture in the garment. The method further comprises emitting a sensorially perceivable indicia from the moisture detection module upon occurrence of sensed moisture in the garment.

Yet another broad object of embodiments can be a method of using a moisture detection article which includes securing a moisture detection module to a garment, disposing the moisture sensor at a location in the garment to sense moisture, positioning the garment on a wearer, and initializing the moisture detection module secured to the garment. The moisture detection module includes a processor communicatively coupled to a non-transitory computer readable medium containing computer executable instructions executable to receive moisture sensor signals generated by the moisture sensor, analyze the moisture sensor signals received from the moisture sensor, detect the moisture in the garment based on analysis of the moisture sensor signals, validate detection of the moisture in the garment, and activate a moisture indicator which emits a sensorially perceivable indicia upon detection of the moisture in the garment. The method further comprises re-initializing the moisture detection module to disable the moisture indicator and interrupt emission of the sensorially perceivable indicia.

Naturally, further objects of the invention are disclosed throughout other areas of the specification, drawings, photographs, and claims.

IV. DETAILED DESCRIPTION

Generally, embodiments of a moisture detection module and methods for detecting moisture are described herein and illustrated in the accompanying figures. Specifically, embodiments of a moisture detecting garment including a garment and a moisture detection module secured to a garment. The garment can be worn in a configuration to capture body fluids originating from the garment wearer. The moisture detection module can include a moisture sensor disposable in the garment to detect occurrence of moisture in the garment. Upon moisture detection, the moisture detection module can activate one or more moisture indicators to correspondingly emit one or more sensorially perceivable indicia. In particular embodiments, a moisture absorbent material can be removably affixed to the garment. The moisture absorbent material can capture moisture inside of the garment and be released from the garment to remove captured moisture from the garment.

Figure 1:
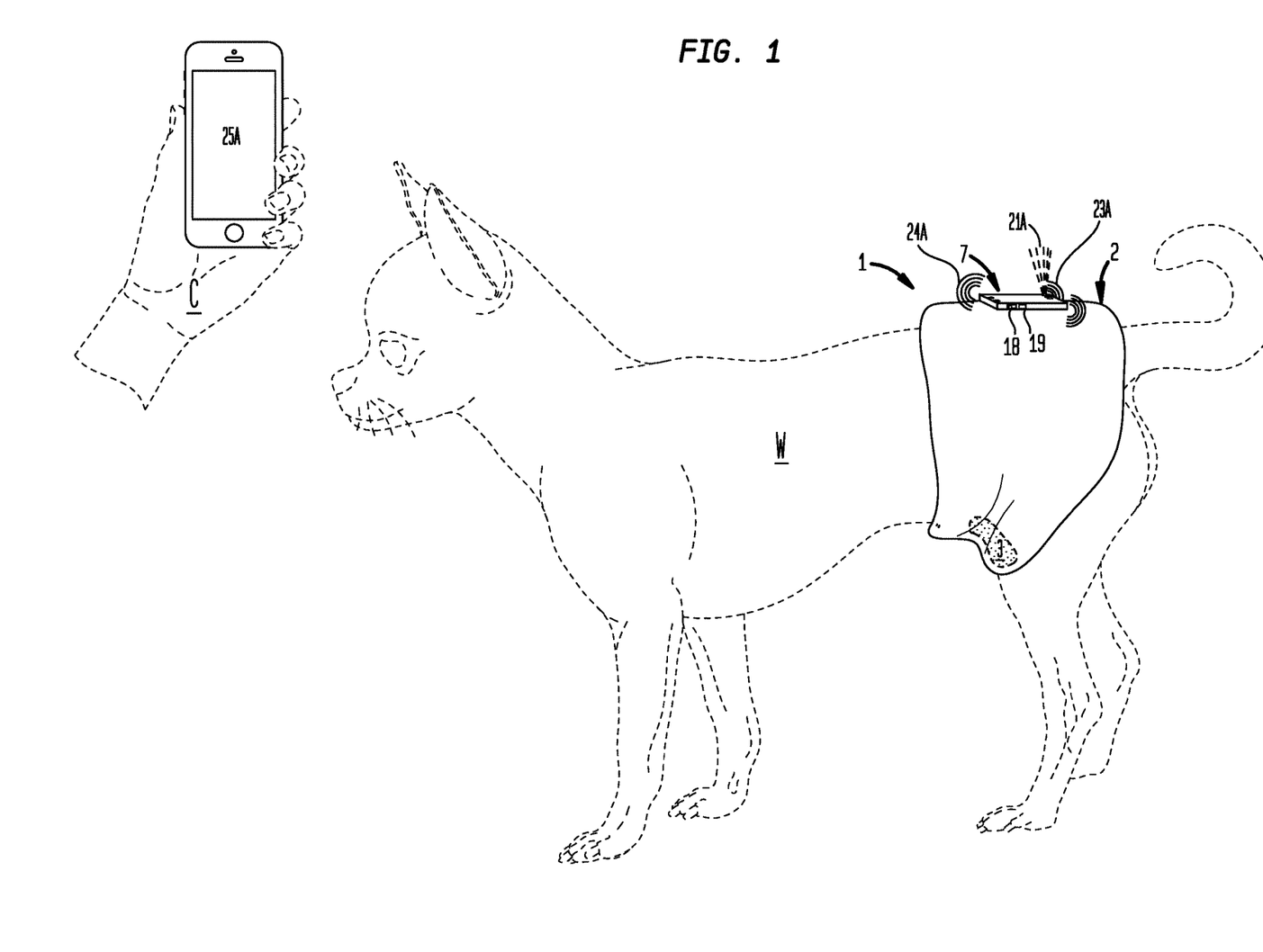
FIG. 1 is a perspective view of an embodiment of a moisture detecting article worn by a garment wearer.

Now referring to the figures wherein like reference numerals denote like structure throughout the specification, with reference primarily to FIG. 1 which depicts a moisture detecting article (1) which, can but need not necessarily, include a garment (2) and moisture detection module (7), as worn by wearer (W) to detect moisture (3) occurring in the garment (2). In the example of FIG. 1, the wearer (W) can be an animal, such as, a dog or a cat. However, this illustrative example is not intended to preclude embodiments of the moisture detecting article (1) which can be worn by either non-human or human animals. The moisture detection module (7) can have applications outside the scope of garment (2). In regard to moisture detection garments, the term "moisture" means a body fluid (or combinations of body fluid) originating from the wearer (W) (whether human or non-human) such as: urine, feces, saliva, blood, breast-milk, mucus, vaginal secretion, semen, amniotic fluid, or vomit.

Figure 2A:
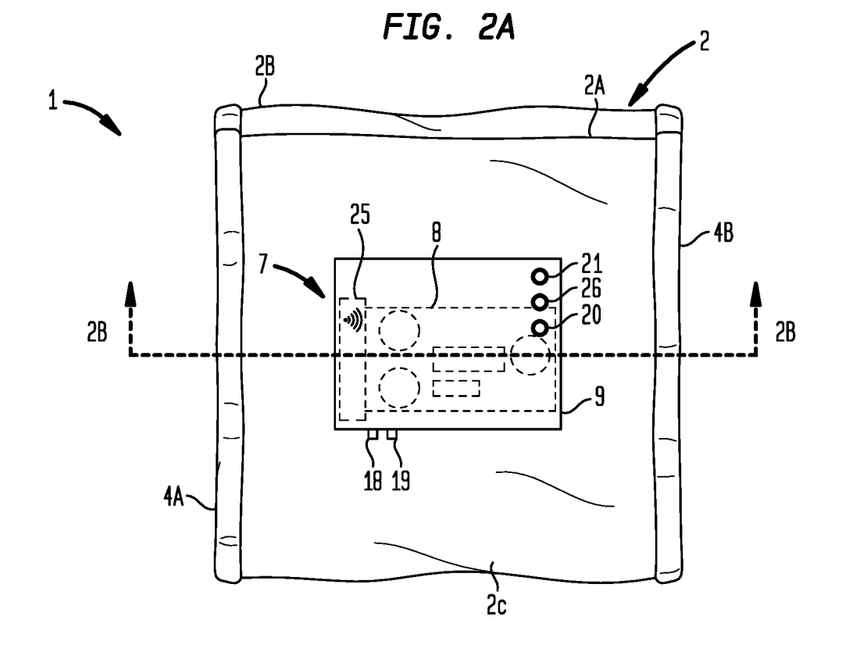
FIG. 2A is a top view of an embodiment of a moisture detecting article.
Figure 2B:
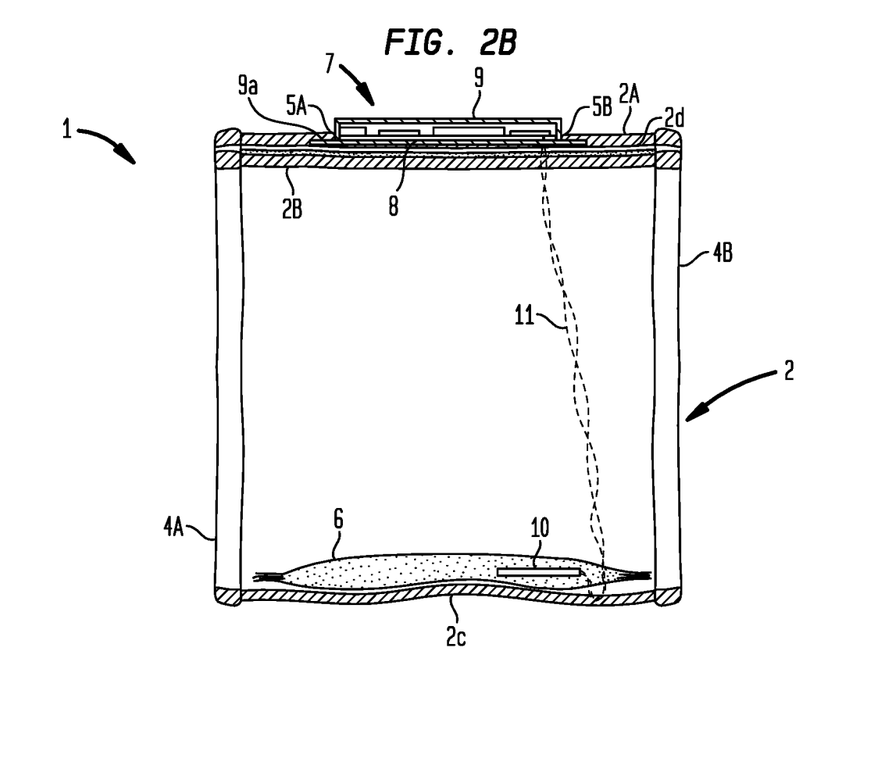
FIG. 2B is a side sectional view of an embodiment of a moisture detecting article.

Now referring primarily to FIG. 2A and FIG. 2B, the garment (2) can, but need not necessarily, be made of a moisture absorbent material. Garment (2) can be comfortable for the wearer (W) as well as sanitary and washable. The garment (2) can be a wrap type article having a medial portion (2C) disposed between a first end portion (2A) which releasably fastens to a second end portion (2B). While the embodiment shown in FIGS. 2A and 2B illustrate use of hook and loop fasteners (2D) to releasably fasten the first end portion (2A) to the second end portion (2B), various other fasteners known in the art can be used to fasten first and second end portions (2A)(2B) to secure the garment (2) to the wearer (W).

In particular embodiments, the garment (2) can, but need not necessarily, include elasticized trim (4A, 4B) on the peripheral edges of the garment (2) which can elastically conform to the wearer (W). The garment (2) can be made from various materials including or consisting of: synthetic fibers, such as polyester, acrylic, nylon, rayon, acetate, spandex, latex, Orlon®, Kevlar®, or the like, or natural fibers such as: wool, cashmere, cotton, silk, linen, hemp, or the like, or in various combinations thereof, either as one layer or joined as a plurality of layers, or combinations thereof.

Various fasteners, straps, clips or hooks, or combinations thereof, can be used to secure the moisture detection module (7) to the garment (2). In the particular embodiment shown in FIGS. 2A and 2B, the external casing (9) of the moisture detection module (7) includes an outwardly extending peripheral margin (9A) removably insertable into slits (5A, 5B) corresponding located in the garment (2). In particular embodiments, the external casing (9) of the moisture detection module (7) can be secured to the garment (2) at location that does not allow the wearer (W) to remove the moisture detection module (7) from the garment (2). In the illustrative example of a wearer (W) being pet animal, the garment (2) can be wrapped about the pet animal with first and second end portions (2A), (2B) fastened in overlapping engagement over the top line of the pet animal and the medial portion (2C) disposed about the belly of the pet animal (as shown in the illustrative example of FIG. 1) and the moisture detection module (7) can be secured to the garment (2) near the overlapping engagement of the first and second end portions (2A), (2B) of the garment (2). With respect to pet animals such as dogs or cats, this location of the moisture detection module (7) can be unreachable by mouth and paws, and provides ready access to the moisture detection module (7) by the pet animal's caretaker (C) to secure, detach, and re-secure the moisture detection module (7) to the garment (2).

With continuing reference to FIG. 2B, embodiments can, but need not necessarily, include a moisture absorbent material (6) removably affixable to the garment (2). In particular embodiments, the moisture absorbent material (6) can be obtained as conventional disposable diapers or a liner pads. Various other moisture absorbent materials (6) may be used for greater or lesser absorbency depending on the application such as silica gel, clay, calcium chloride, or the like.

Figure 3:
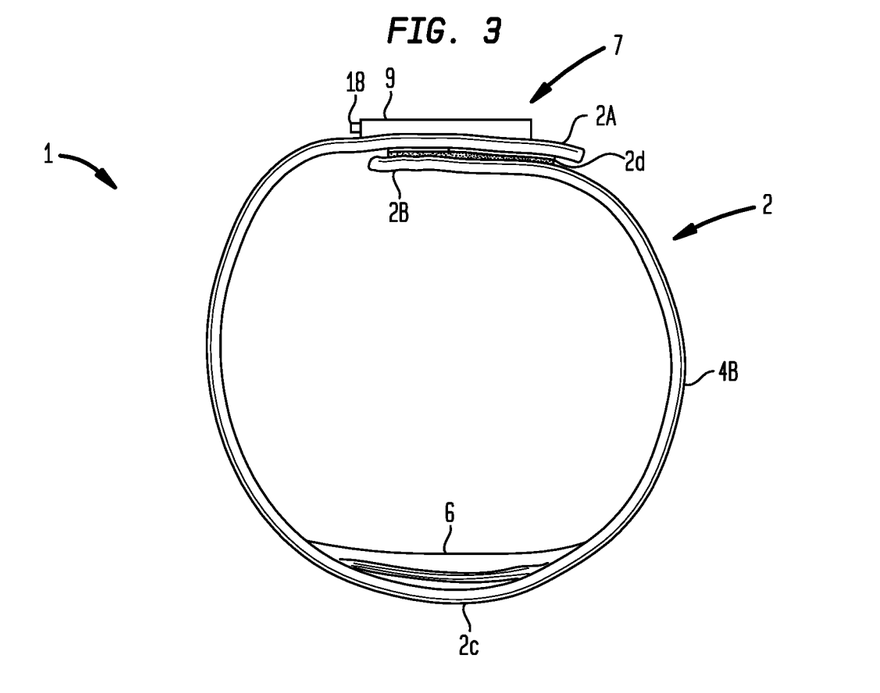
FIG. 3 is a front end view of an embodiment of a moisture detecting article.
Figure 4:
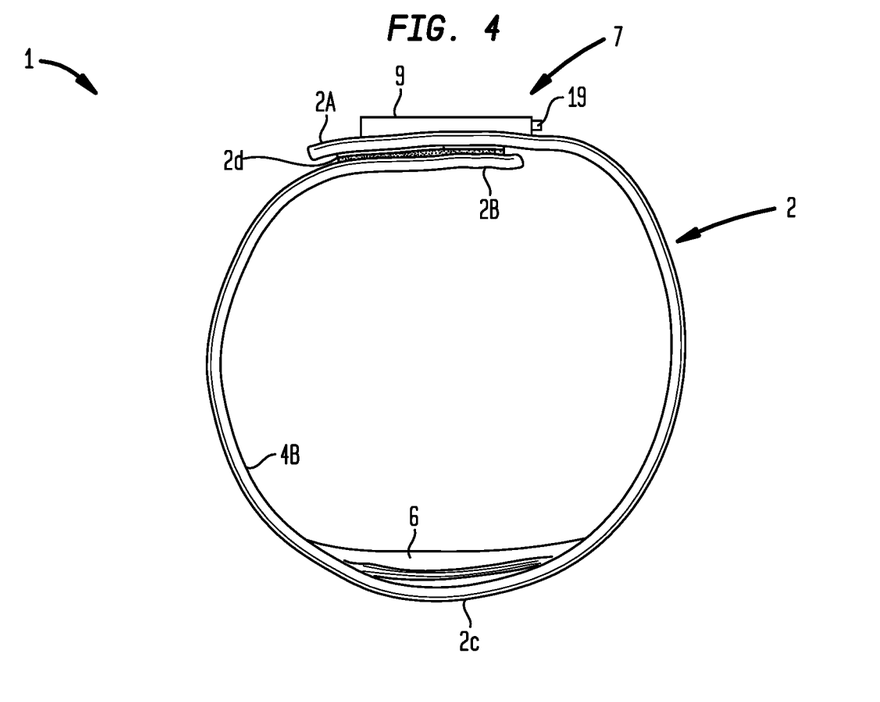
FIG. 4 is a rear end view of an embodiment of a moisture detecting article.
Figure 5:
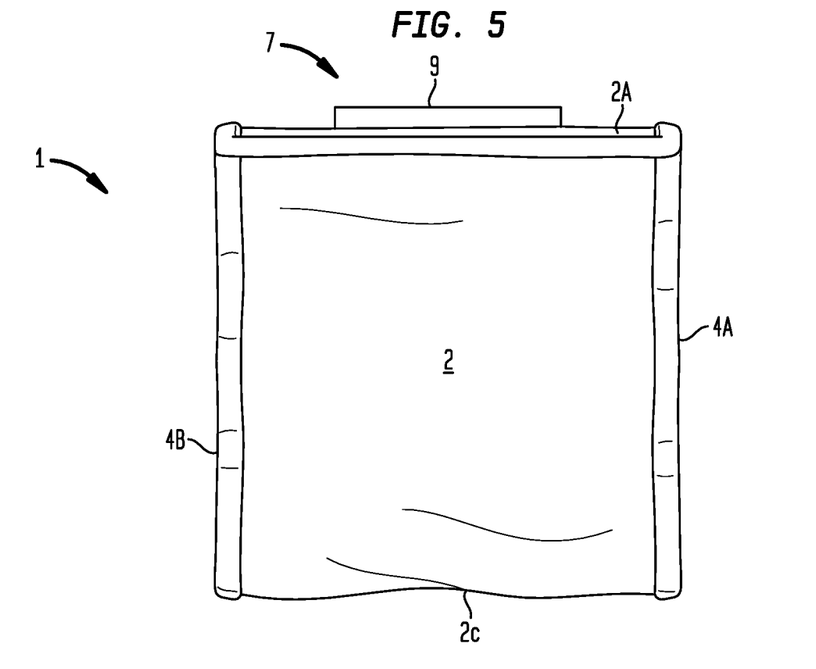
FIG. 5 is a left side view of an embodiment of a moisture detecting article.
Figure 6:
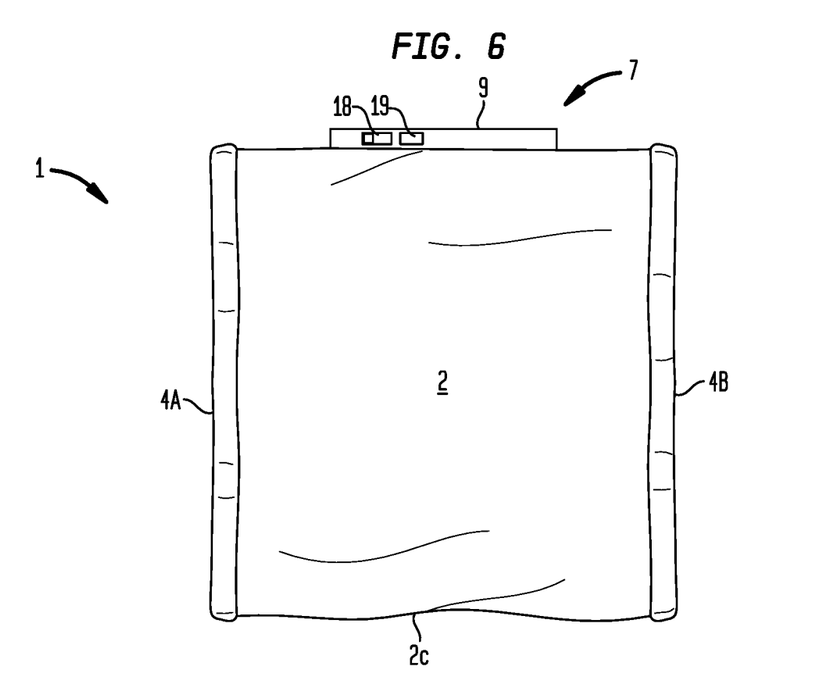
FIG. 6 is a right side view of an embodiment of a moisture detecting article.
Figure 7:
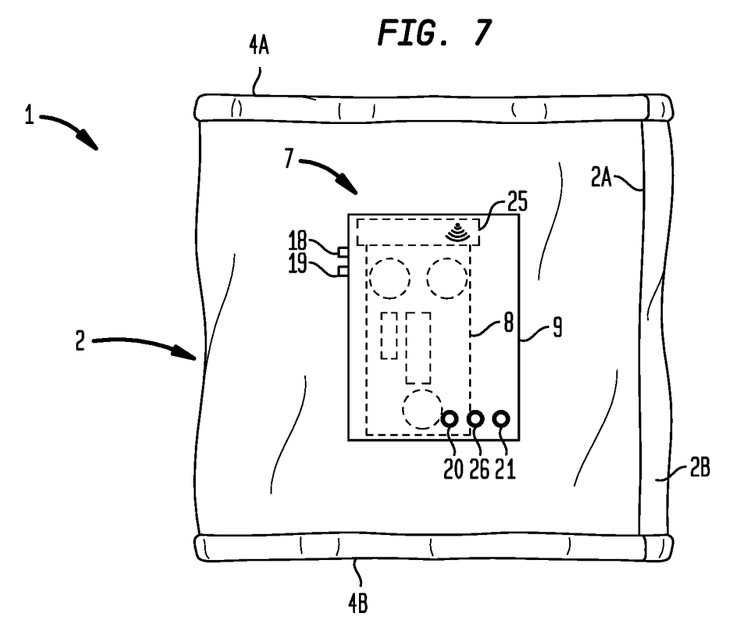
FIG. 7 a top view of an embodiment of a moisture detecting article.
Figure 8:
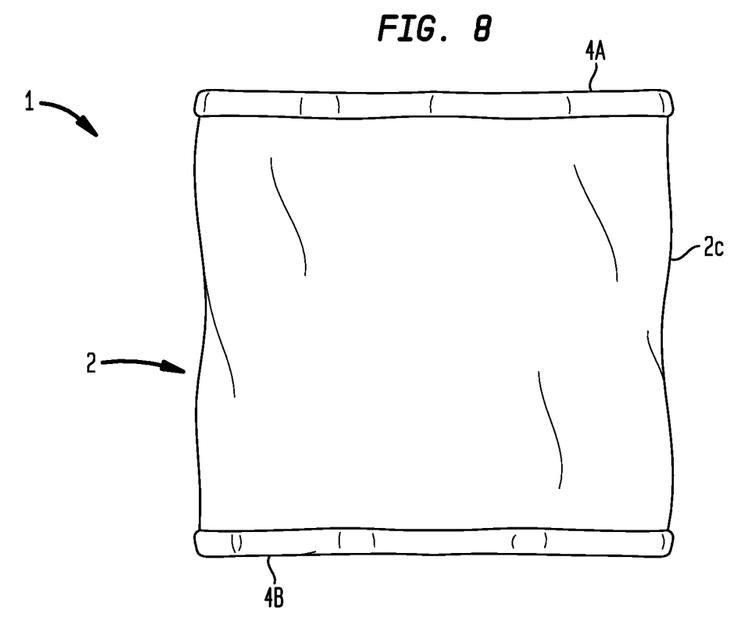
FIG. 8 is a bottom view of an embodiment of a moisture detecting article.

Now referring primarily to FIG. 3 and FIG. 4, moisture absorbent material (6) can be detachably secured to the garment (2) near specific anatomical locations of the wearer (W) to receive and capture moisture (3) in the form of body fluid. Various other fasteners, straps, and hooks can be used to secure the moisture absorbent material (6) to the garment (2).

Now referring primarily to FIGS. 5 through 8, embodiments of the moisture detection module (7) can include a circuit board (8) disposed in external casing (9). In the embodiment shown in FIG. 7, certain elements can pass through the external casing (9) such as an on/off switch (18) and a reset switch (19) or be viewable through the external casing (9) such as a power indicator (26), low battery indicator (20), or moisture indicator (21).

Figure 9:
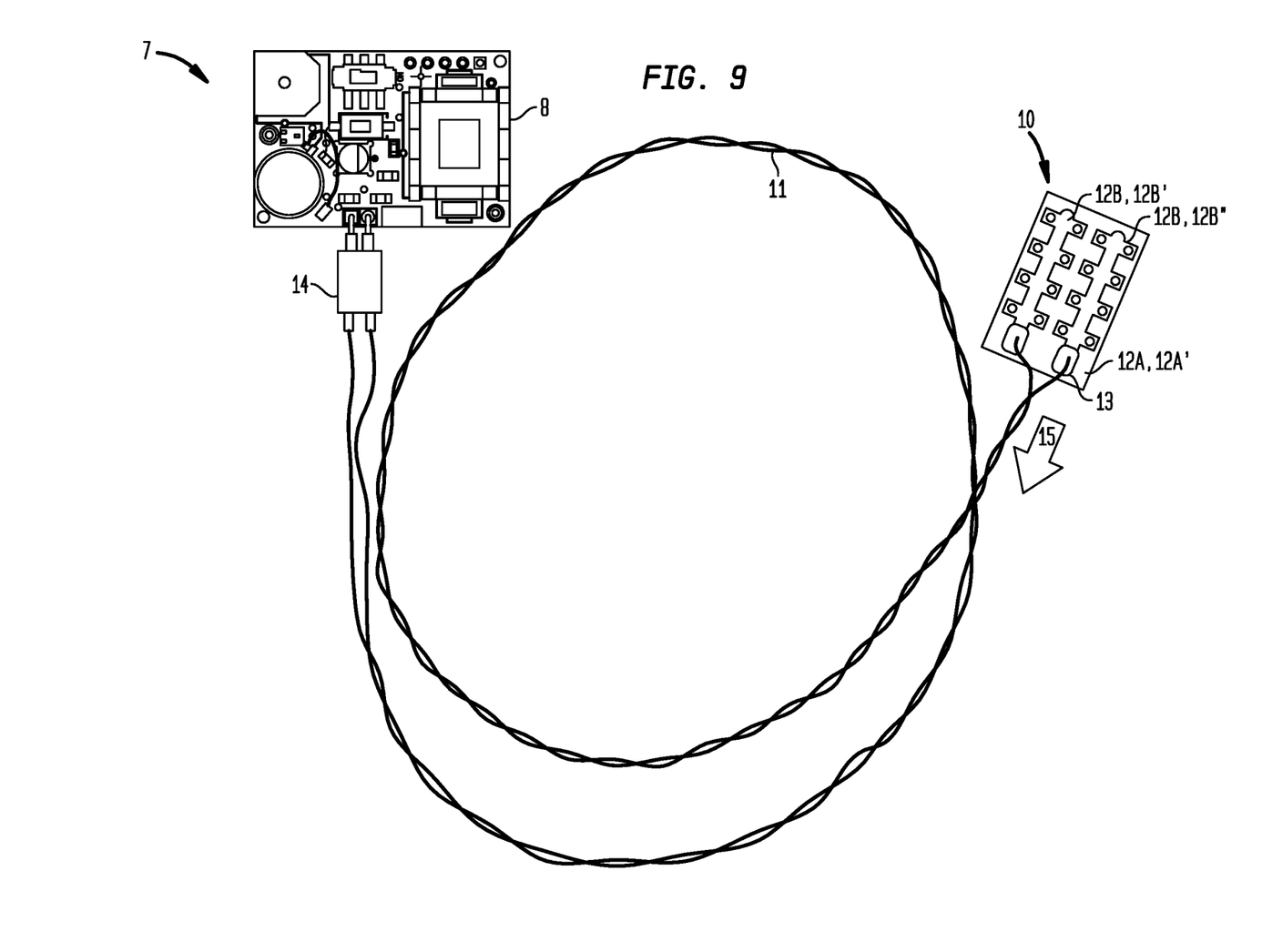
FIG. 9 illustrates an embodiment of a moisture detection module electrically coupled to a moisture sensor.

Referring primarily to FIG. 9, particular embodiments of the moisture detection module (shown without the external casing (9)) can further include a moisture sensor (10) made from thin and flexible non-conductive, but not extendable or compressible substrate (also referred to as the "substrate") (12A). Such flexible and non-conductive substrates can include or consist of: a polyimide, a polyester, a silicone, and other suitable material, or combinations thereof. Moisture sensor (10) can be substantially flat, yet conformable to the configuration of the garment (2) or the moister absorbent material (6) when worn by the wearer (W). The substrate (12A) of the moisture sensor (10) affords a substrate surface area (12A') which can be substantially adjusted to be greater or lesser in area depending on the application due the nature of the flexible substrate (12A).

Again, referring primarily to FIG. 9, an embodiment of the moisture sensor (10) includes one or more moisture sensing strips (12B) laid down on the substrate (12A). The sensing strips (12B) can be an array of capacitive-based sensing elements. In the particular embodiment shown in FIG. 9, the sensing elements take the form of two generally planar electrodes (12B')(12B") of an open-face virtual capacitor. In particular embodiments, the sensing strips (12B) can be laid down on the substrate (12A) by etching of a silver sheet laminated onto the substrate (12A).

With continuing reference primarily to FIG. 9, moisture detection module (7) further includes a sensor conductor (11), which connects the moisture sensor (10) to the circuit board (8) by way of interface (13) and connector (14). Any suitable type of interface or connector can be used, depending on the number of sensing strips (12B) laid down on the moisture sensor (10). For example, in particular embodiments, interface (13) can be a USB bundled type connection, and connector (14) can be a zero-insertion force connector or any other suitable connector.

Figure 10:
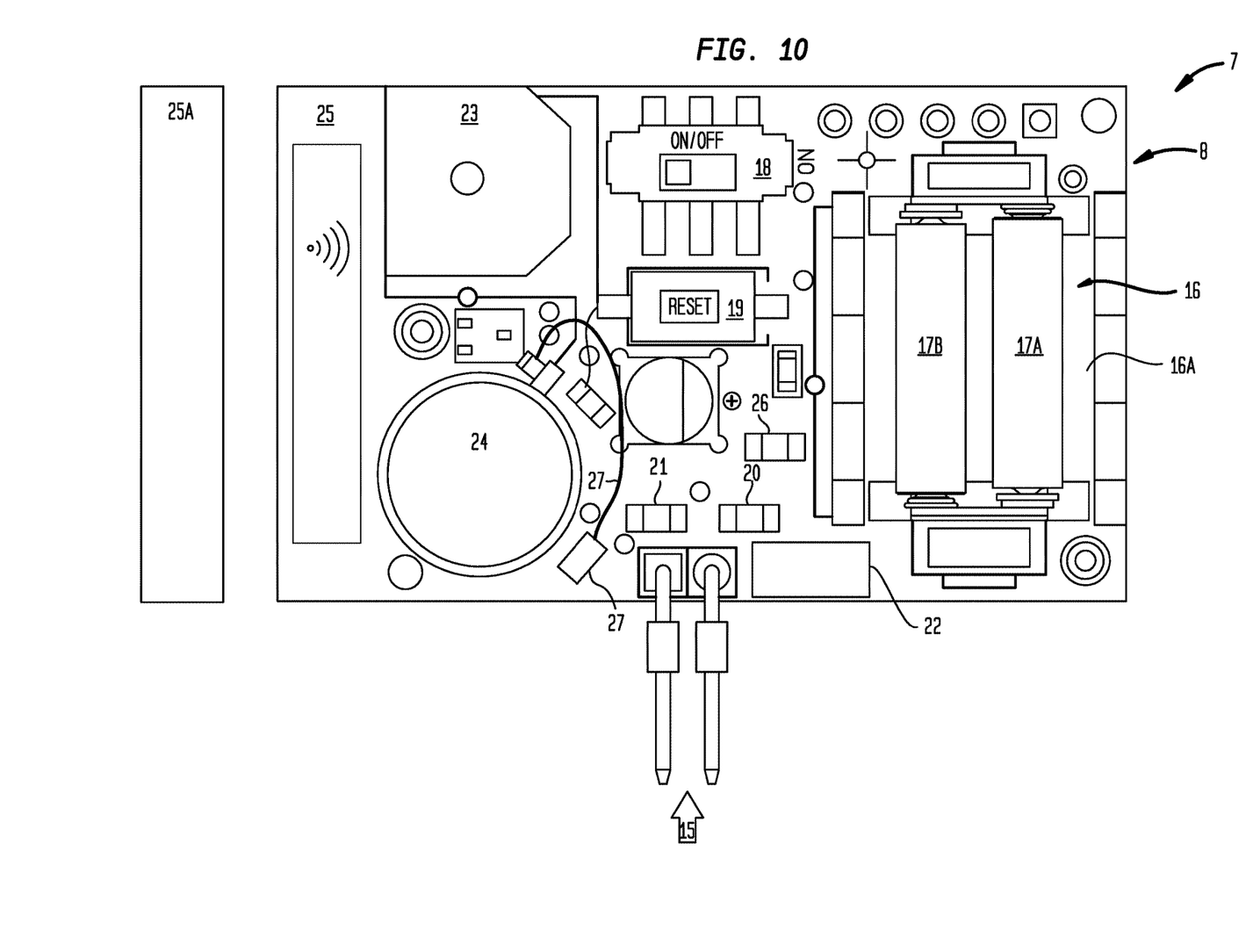
FIG. 10 is a top, plan view of an embodiment of a moisture detection module.
Figure 11:
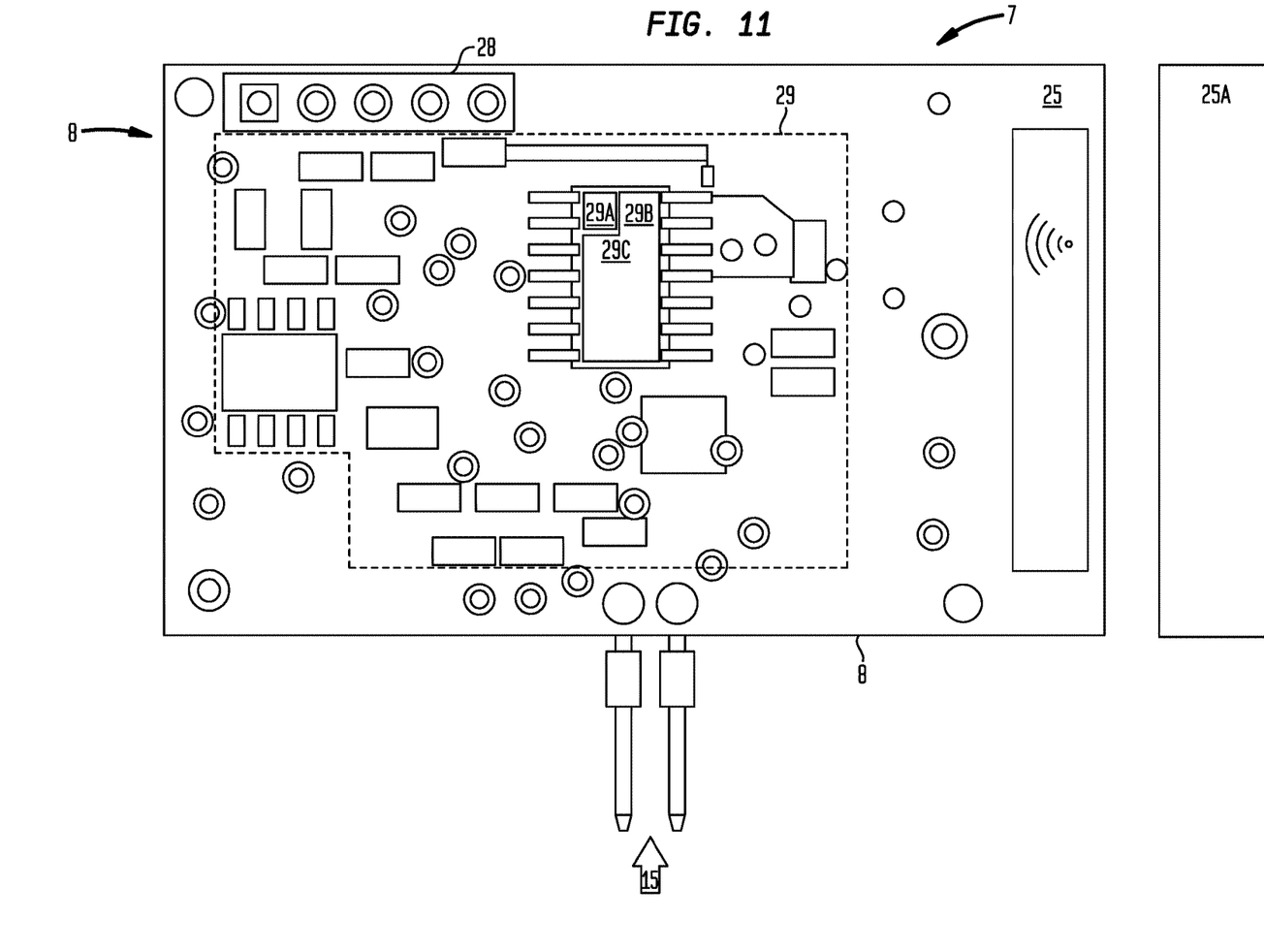
FIG. 11 is a bottom, plan view of an embodiment of a moisture detection module.

Now referring primarily to FIGS. 10 and 11, circuit board (8) can, but need not necessarily, be a two-sided substrate (a first side shown in FIG. 10 and a second side shown in FIG. 11). In particular embodiments, the first side of the circuit board (8) can support a power source (16). The power source (16) shown in the example of FIG. 10 includes a battery holder (16A) adapted to electrically couple batteries (17A, 17B). The first side of circuit board (8) can further support, at least one moisture indicator (21), (23), or (24). In particular embodiments, the at least one moisture indicator (21), (23) or (24) can respectively take the form of a light emitting element (21) which emits a sensorially perceivable amount of light (21A) to either the garment wearer (W) or the caretaker (C) (as shown in the example of FIG. 1), a sound emitting element (23) which emits a sensorially perceivable amount of sound (23A) to garment wearer (W) or the caretaker (C) (as shown in the example of FIG. 1), and a vibration emitting element (24) which emits a sensorially perceivable amount of vibration (24A) to the garment wearer (W) or the caretaker (C) (as shown in the example of FIG. 1). The light emitting element (21) can, but need not necessarily, be a light emitting diode. In particular embodiments, the light emitting element (21) can, but need not necessarily, be color coded by emitted wavelength or light emitting element cover (as one example perceivable as red colored) to distinguish this moisture indicator (21) from other light emitting elements such as a power status indicator (26) (as one example perceivable as green colored) or a low power level indicator (20)(for example perceivable as yellow or orange). In particular embodiments, the vibration emitting element (24) can be an eccentric rotating mass motor available from Digikey, PN 159701244. In particular embodiments, the sound emitting element (23) can, but need not necessarily, be an alerts buzzer available from Mouser Electronics, PN CMI-9643-SMT-TR. These illustrative examples of moisture indicators (21), (23) and (24) are not intended to preclude embodiments which incorporate similar or equivalent indicators, or other indicators, currently or prospectively available. For example, the sound emitting element (23) could also take the form of piezoelectric speaker, an electrodynamic speaker, miniature speaker including a mylar cone and plastic frame such as PSR-13N08A-JQ available from PUI Audio.

Again, referring primarily to FIG. 10, the first side of circuit board (8) can further support a power status indicator (26) which illuminates to indicate the power "on" condition of the moisture detection module (7) and a low power level indicator (20) which illuminates to indicate a low power level condition of the power source (16). Both the power status indicator (26) and the low power lever indicator (20) can, but need not necessarily, be light emitting diodes.

Again, referring primarily to FIG. 10, the first side of circuit board (8) can further support a tail-pin header sensor system (27), as well as a vibration emitter engage/shunt (22).

Again, referring primarily to FIG. 10, the circuit board (8) can further include an on/off switch (18) and a reset button (19). In particular embodiments, either one or both of the on/off switch (18) and the reset button (19) can be positioned for accessibility on a sidewall of the casing (9)(as show in the example of FIG. 7) rather than in an upward-facing direction from the circuit board (8)(as shown in the example of FIG. 10).

Again, referring primarily to FIG. 10, embodiments can, but need not necessarily, include a communications subsystem (25) which wirelessly connects to any of a plurality of commercially available client systems (25A) used by a caretaker (C). The communications subsystem (25) can communicate with any one of, or any combination of, one or more Local Area Networks (LANs), Wide Area Networks (WANs), wireless networks, telephone networks, the Internet and/or other networks.

With continuing reference, primarily to FIG. 10, particular embodiments can, but need not necessarily, include a communications subsystem (25) having one or more wireless portals, for example, BLUETOOTH® or WI-FI® technology. A client system (25A) can be used to access or communicate with the communications subsystem (25). For example, client systems (25A) can include or consist of: personal computers, workstations, laptop computers, game consoles, handheld network enabled audio/video players or combinations thereof. Client systems (25A) can include handheld wireless devices, including or consisting of: a mobile phone or a handheld network enabled audio/music player, which may also be used for accessing network content. The client systems (25A) can also be utilized in combination with a handheld wireless device application (25B) from any available application source provider, such as the App Store by Apple®.

Now referring primarily to FIG. 11, embodiments can further include a microprocessor system (29) which manages data and controls operation of the moisture detection module (7). In particular embodiments of the moisture detecting module (7), microprocessor system (29) includes a processor (29A) communicatively coupled to a non-transitory computer readable medium (29B) containing computer-executable instructions (29C). Microprocessor system (29) can, as an illustrative example, include one or more elements disposed on the circuit board (8) for storing data as a non-transitory computer readable media. The elements of the non-transitory computer readable medium can be formed as an integrated circuit or chip having flash memory or any other type of memory structure for storing data. In various embodiments, microprocessor system (29) of the moisture detecting article (1) can include any of various types of memory devices or storage devices, controllers, timers, input/output ports, counters, and interrupters or re-interrogators.

Again, referring primarily to FIG. 11, in addition, the microprocessor system (29) can be communicatively coupled via communications subsystem (25) to a client system (25A), as referred above, in which the plurality of client systems (25A) are connected to one another over a network, such as the Internet. In some embodiments, communication protocols, included as part of communications subsystem (25), can be used for physically and communicatively coupling the moisture detection module (7) to a client system (25A), such as a computing device, in order to facilitate data transfer between the moisture detection module (7) and the computing device. Communications subsystem (25), in addition to the descriptions above, can include a physical transmission medium, such as a bus, network, or other physical transmission medium that conveys signals such as electrical, electromagnetic, or digital signals.

Again, referring primarily to FIG. 11, in some embodiments, microprocessor system (29) can be a non-transitory computer readable medium (29B) containing computer executable instructions (29C) executable to activate at least one moisture indicator (21, 23, 24)(as shown in the example of FIG. 10) which emits a sensorially perceivable indicia (21A, 23A, 24A) upon detection of moisture (3) in the garment (2) (as shown in the example of FIG. 1). The computer executable instructions (29C) are further executable to receive moisture sensor signals (15) generated by the moisture sensor (10), analyze the moisture sensor signals (15) received from the moisture sensor (10), detect the moisture (3) in the garment (2) based on analysis of the moisture sensor signals (15), and validate detection of the moisture (3) in the garment (2).

Still referring primarily to FIG. 11, microprocessor system (29), in various embodiments, can be a non-transitory computer readable medium (29B) containing computer executable instructions (29C) executable to activate each of the plurality of the moisture indicators (21, 22, 23) and deactivate each of the plurality of the moisture indicators (21, 22, 23) upon elapse of a period of time. Light emitting element (21) can, but need not necessarily, remain activated until deactivated by a caretaker (C) interaction with the reset switch (19).

Various embodiments further include receiving or storing instructions or data implemented in accordance with the foregoing description of the microprocessor system (29) and the moisture detecting article (1).

Figure 12:
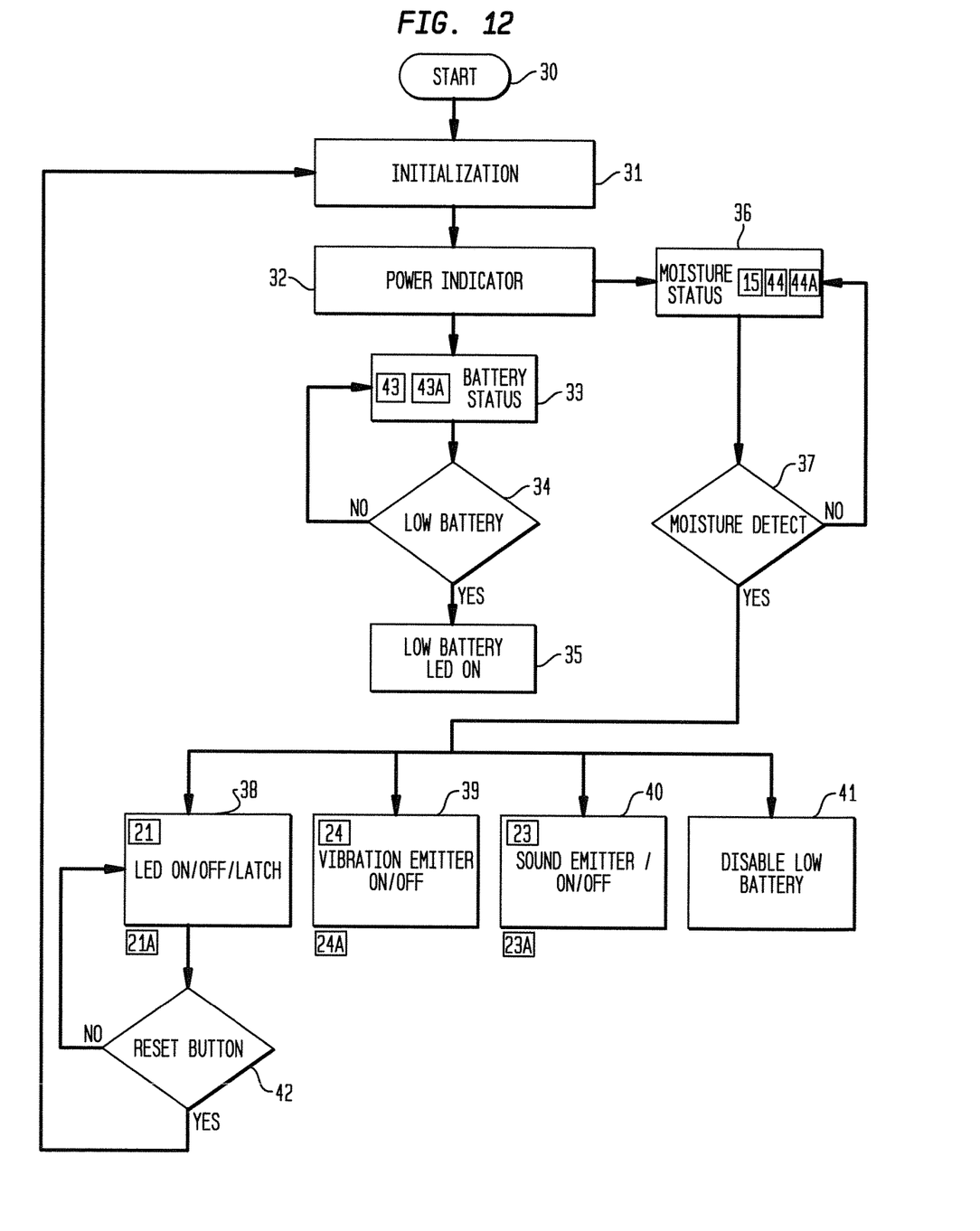
FIG. 12 is a decision-based flow diagram illustrating operation of an embodiment of a moisture detection module.

Now referring primarily to FIG. 12, microprocessor system (29) of the moisture detection module (7) can include a processor (29A) communicatively coupled to a non-transitory computer readable medium (29B) containing computer executable instructions (29C) (also referred to as "instructions")(as shown in the example of FIG. 11) executable to operate the moisture detection module (7). The illustrative operation of the moisture detection module (7) shown in FIG. 12 is not intended to preclude embodiments only included a portion of the operations shown or to preclude embodiments in which all or portions of the operations shown are performed in a different order. In one embodiment, operation of the moisture detection module (7) can include a start sequence (30) which includes placing the on/off switch (18) in the "on" condition to supply power to the moisture detection module (7). Upon start (30), the microprocessor system (29) can follow an initialization sequence (31) which assigns initial values or default values to data variables. The manner in which the initialization sequence (31) is performed depends on programming language, as well as type, storage class of the data variable to be initialized. In particular embodiments, operation (32) further includes execution of instructions (29C) to activate the power status indicator (26), and in particular embodiments, the power status indicator (26) can be activated and then deactivated upon elapse of a period of time (for example, the power status indicator (26) can be turned on for ten seconds then turned off). In particular embodiments, operation (33) further includes execution of instructions (29C) to assess a power level value (43) of the power source (16) electrically connected to the moisture detection module (7), compare the power level value (43) of the power source (16) to a low power level value (43A), and in operation (34) if the power level value (43) is less than the low power level value (43A), operation (35) can include execution of instructions (29C) to activate the low power level indicator (20).

Again, referring primarily to FIG. 12, in particular embodiments, the microprocessor system (29) moisture detection module (7) can further operate (36) to execute instructions (29C) to receive moisture sensor signals (15) generated by the moisture sensor (10). In particular embodiments, the moisture sensor signals (15) can vary based upon the mutual capacitance between adjacent planar electrodes (12B')(12B") of the moisture sensing strips (12) or self-capacitance of one of the moisture sensing strips (12). Operation (36) can further include execution of instructions (29C) to analyze moisture sensor signals (15) received from said moisture sensor (10). Analysis can, but need not necessarily, include a mutual or self-capacitance measurement and comparison of a mutual or self-capacitance value (44) against a moisture detection capacitance value (44A). If the mutual or self-capacitance value (44) is greater than the moisture detection capacitance value (44A), then further operation (37) detects moisture (3) inside of said garment (2) based on analysis of said moisture sensor signals (15).

Again, referring primarily to FIG. 12, in particular embodiments, operation (36) can further include execution of instructions (29C) to validate detection of moisture (3) inside of the garment (2). To validate detection of moisture (3) inside of the garment (2) the moisture sensor signals (15) and measured mutual or self-capacitance value (44) can be re-analyzed against the moisture detection capacitance value (44A) over a period of time, or the moisture sensor (10) can be interrogated a pre-determined number of times, and if the mutual or self-capacitance value (44) continues to be greater than the moisture detection capacitance value (44A) over the period of time repeated interrogations, then further operation (37) detects moisture (3) inside of the garment (2). Upon detection of moisture (3) inside of the garment (2), the moisture detection module (7) can further perform one or more of operations (38), (39), or (40) activating at least one moisture indicator (21), (23), (24) which emits a sensorially perceivable indicia (21A), (23A), (24A), respectively, upon detection of said moisture (3) in the garment (2). In particular embodiments, operation (38) activates a light emitting element (21) which emits a sensorially perceivable amount of light (21A) to either the garment wearer (W) or the caretaker (C). In particular embodiments, operation (39) activates a vibration emitting element (24) which emits a sensorially perceivable amount of vibration (24A) to the garment wearer (W) or the caretaker (C). In particular embodiments, operation (40) activates a sound emitting element (23) which emits a sensorially perceivable amount of sound (23A) to the garment wearer (W) or the caretaker (C). In particular embodiments, two or more of operations (38), (39) or (40) can occur concurrently for a period of time. In particular embodiments, operations (38), (39) and (40) can occur concurrently for a period of time, and upon elapse of the period of time, operations (39) and (40) can be discontinued and operation (38) can continue until operation (42) is performed. Operation (42) includes operation of the reset switch (19) upon which the microprocessor system (29) executes instructions (29C) to perform operation (31) and deactivate the light emitting element (21). The garment wearer (W) or the caretaker (C) can operate the reset switch (19). In particular embodiments, when operation (35) activates the low power indicator (22) concurrent with one or more of operations (38), (39), or (40), the moisture detection module (7) can further operate (41) to execute instructions (29C) which disables operation (35) to deactivate the low power indicator (22).

Various embodiments further include use and operation sequences or data implemented in accordance with the foregoing description of the moisture detecting article (1).

As can be easily understood from the foregoing, the basic concepts of the present invention may be embodied in a variety of ways. The invention involves numerous and varied embodiments of a moisture detecting article, a moisture detection module, a method of moisture detection, a method of using a moisture detecting article, and the component parts thereof, including the best mode.

As such, the particular embodiments or elements of the invention disclosed by the description or shown in the figures or tables accompanying this application are not intended to be limiting, but rather exemplary of the numerous and varied embodiments generically encompassed by the invention or equivalents encompassed with respect to any particular element thereof. In addition, the specific description of a single embodiment or element of the invention may not explicitly describe all embodiments or elements possible; many alternatives are implicitly disclosed by the description and figures.

It should be understood that each element of an apparatus or each step of a method may be described by an apparatus term or method term. Such terms can be substituted where desired to make explicit the implicitly broad coverage to which this invention is entitled. As but one example, it should be understood that all steps of a method may be disclosed as an action, a means for taking that action, or as an element which causes that action. Similarly, each element of an apparatus may be disclosed as the physical element or the action which that physical element facilitates. As but one example, the disclosure of an "indicator" should be understood to encompass disclosure of the act of "indicating"— whether explicitly discussed or not—and, conversely, were there effectively disclosure of the act of "indicating", such a disclosure should be understood to encompass disclosure of an "indicator" and even a "means for indicating." Such alternative terms for each element are to be understood to be explicitly included in the description.

In addition, as to each term used it should be understood that unless its utilization in this application is inconsistent with such interpretation, common dictionary definitions should be understood to be included in the description for each term as contained in the Random House Webster's Unabridged Dictionary, second edition, each definition hereby incorporated by reference.

All numeric values herein are assumed to be modified by the term "about", whether or not explicitly indicated. For the purposes of the present invention, ranges may be expressed as from "about" one particular value to "about" another particular value. When such a range is expressed, another embodiment includes from the one particular value to the other particular value. The recitation of numerical ranges by endpoints includes all the numeric values subsumed within that range. A numerical range of one to five includes for example the numeric values 1, 1.5, 2, 2.75, 3, 3.80, 4, 5, and so forth. It will be further understood that the endpoints of each of the ranges are significant both in relation to the other endpoint, and independently of the other endpoint. When a value is expressed as an approximation by use of the antecedent "about," it will be understood that the particular value forms another embodiment. The term "about" generally refers to a range of numeric values that one of skill in the art would consider equivalent to the recited numeric value or having the same function or result. Similarly, the antecedent "substantially" means largely, but not wholly, the same form, manner or degree and the particular element will have a range of configurations as a person of ordinary skill in the art would consider as having the same function or result. When a particular element is expressed as an approximation by use of the antecedent "substantially," it will be understood that the particular element forms another embodiment.

Moreover, for the purposes of the present invention, the term "a" or "an" entity refers to one or more of that entity unless otherwise limited. As such, the terms "a" or "an", "one or more" and "at least one" can be used interchangeably herein.

Thus, the applicant(s) should be understood to claim at least: i) the moisture detecting article disclosed and described, ii) each of the related methods disclosed and described, iii) similar, equivalent, and even implicit variations of each of the article and methods, iv) those alternative embodiments which accomplish each of the functions shown, disclosed, or described, v) those alternative designs and methods which accomplish each of the functions shown as are implicit to accomplish that which is disclosed and described, vi) each feature, component, and step shown as separate and independent inventions, vii) the applications enhanced by the various systems or components disclosed, viii) the resulting products produced by such systems or components, ix) methods and apparatuses substantially as described hereinbefore and with reference to any of the accompanying examples, x) the various combinations and permutations of each of the previous elements disclosed.

The background section of this patent application provides a statement of the field of endeavor to which the invention pertains. This section may also incorporate or contain paraphrasing of certain United States patents, patent applications, publications, or subject matter of the claimed invention useful in relating information, problems, or concerns about the state of technology to which the invention is drawn toward. It is not intended that any United States patent, patent application, publication, statement or other information cited or incorporated herein be interpreted, construed or deemed to be admitted as prior art with respect to the invention.

The claims set forth in this specification, if any, are hereby incorporated by reference as part of this description of the invention, and the applicant expressly reserves the right to use all of or a portion of such incorporated content of such claims as additional description to support any of or all of the claims or any element or component thereof, and the applicant further expressly reserves the right to move any portion of or all of the incorporated content of such claims or any element or component thereof from the description into the claims or vice-versa as necessary to define the matter for which protection is sought by this application or by any subsequent application or continuation, division, or continuation-in-part application thereof, or to obtain any benefit of, reduction in fees pursuant to, or to comply with the patent laws, rules, or regulations of any country or treaty, and such content incorporated by reference shall survive during the entire pendency of this application including any subsequent continuation, division, or continuation-in-part application thereof or any reissue or extension thereon.

Additionally, the claims set forth in this specification, if any, are further intended to describe the metes and bounds of a limited number of the preferred embodiments of the invention and are not to be construed as the broadest embodiment of the invention or a complete listing of embodiments of the invention that may be claimed. The applicant does not waive any right to develop further claims based upon the description set forth above as a part of any continuation, division, or continuation-in-part, or similar application.

What is claimed is:

1. A moisture detection apparatus, comprising:
a moisture detector securable to an article, said moisture detector including:
a moisture sensor adapted upon securement to said article to sense moisture within said article, said moisture sensor generating moisture sensor signals upon occurrence of said moisture in said article; and
a processor communicatively coupled to a non-transitory computer readable medium containing computer executable instructions executable to activate at least one moisture indicator which emits a sensorially perceivable indicia upon detection of said moisture in said article,
wherein said at least one moisture indicator includes a light emitting element which emits a sensorially perceivable amount of light, a sound emitting element which emits a sensorially perceivable amount of sound, a vibration emitting element which emits a sensorially perceivable amount of vibration.

2. The moisture detector of claim 1, wherein said article comprising a moisture absorbent material removably affixed to said moisture detector, said moisture sensor located to detect said moisture captured by said moisture absorbent material.

3. The moisture detector of claim 2, wherein said moisture absorbent material affixed to a garment.

4. The moisture detector of claim 3, wherein said moisture comprises a body fluid originating from a wearer of said garment.

5. The moisture detector of claim 4, wherein said body fluid is selected from one or more of the group consisting of: urine, feces, saliva, blood, breastmilk, mucus, vaginal secretion, semen, amniotic fluid, and vomit.

6. The moisture detector of claim 1, wherein said computer executable instructions are further executable to:
   repeatedly interrogate said moisture sensor over a pre-determined time period;
   calculate a mutual capacitance or a self-capacitance value of each interrogation of said moisture sensor based on said moisture sensor signals;
   compare said mutual capacitance or said self-capacitance value of each interrogation of said moisture sensor against a moisture detection capacitance value;
   determine if said mutual capacitance or said self-capacitance value of each interrogation of said moisture sensor is greater than said moisture detection capacitance value;
   determine if said mutual capacitance or said self-capacitance value of repeated interrogations of said moisture sensor being greater than said moister detection capacitance value further increases over said time period;
   validate detection of moisture inside of the garment based on said mutual capacitance or said self-capacitance value being greater than said moister detection capacitance value and increases over said time period; and
   activate said at least one moisture indicator which emits a sensorially perceivable indicia upon detection of said moisture.

7. The moisture detector of claim 1, wherein said at least one moisture Indicator comprises a plurality of moisture indicators including a light emitting element which emits a sensorially perceivable amount of light, wherein said computer executable instructions are further executable to activate each of said plurality of moisture indicators and deactivate each of said plurality of said moisture indicators upon elapse of a period of time, said light emitting element remaining activated until deactivated by user interaction with a reset element of said moisture detector.

8. The moisture detector of claim 1, wherein said computer executable instructions are further executable to:
   determine a power level value of a power source electrically connected to said moisture detector;
   compare said power level value of said power source to a low power level value; and
   activate a low power level indicator if said power level value is less than said low power level value.

9. The moisture detector of claim 8, wherein said a low power level indicator comprises a light emitting element comprises a light emitting element which a sensorially perceivable amount of light.

10. The moisture detector of claim 9, wherein said computer executable instructions are further executable to disable determination of said power level of said power source upon activation of said moisture indicator.

11. The moisture detector of claim 1, wherein said computer executable instructions are further executable to re-initialize said moisture detector by user interaction with a reset element electrically connected to said moisture detector.

12. The moisture detector of claim 1, further comprising a transceiver for exchanging data with a remote computing device.

13. The moisture detector of claim 12, wherein said transceiver comprises wireless communication.

14. The moisture detector of claim 13, wherein said computer executable instructions are further executable to transmit notification of detection of said moisture to said remote computing device.

15. The moisture detector of claim 14, wherein said computer executable instructions are further executable to associate a date-time stamp with each said notification of detection of said moisture to said remote computing device.

16. The moisture detector of claim 15, wherein said computer executable instructions are further executable to save each said notification associated with said date-time stamp in a moisture detection log in date-time order retrievable by said remote computing device.

17. The moisture detector of claim 16, wherein computer executable instructions further executable to:
   receive reset instructions from said remote computing device; and
   re-initialize said moisture detector by user interaction with said reset element electrically connected to said moisture detector.

* * * * *